United States Patent [19]

Hoogland et al.

[11] Patent Number: 4,957,497

[45] Date of Patent: Sep. 18, 1990

[54] DEVICE FOR OSTEOSYNTHESIS

[76] Inventors: Thomas Hoogland; Hans E. Harder; Klaus Behrens, all of Pfizer Inc., 235 E. 42nd St., New York, N.Y. 10017

[21] Appl. No.: 380,701

[22] Filed: Jul. 13, 1989

Related U.S. Application Data

[63] Continuation of Ser. No. 233,954, Aug. 18, 1988, abandoned, which is a continuation of Ser. No. 790,713, Oct. 24, 1985, abandoned.

[30] Foreign Application Priority Data

Oct. 27, 1984 [DE] Fed. Rep. of Germany ....... 8431616

[51] Int. Cl.⁵ .............................................. A61F 5/04
[52] U.S. Cl. .......................................... 606/71; 606/60
[58] Field of Search ............ 128/92 Y, 92 YP, 92 PM, 128/92 YF, 92 X; 606/60, 69–72

[56] References Cited

U.S. PATENT DOCUMENTS

| | | | |
|---|---|---|---|
| 2,406,832 | 9/1946 | Hardinge | 128/92 |
| 3,534,731 | 10/1970 | Muller | 128/92 |
| 3,659,595 | 5/1972 | Haboush | 128/92 |
| 3,695,259 | 10/1972 | Yost | 128/92 |
| 4,683,878 | 8/1987 | Carter | 128/92 |

FOREIGN PATENT DOCUMENTS

| | | |
|---|---|---|
| 013862 | 8/1980 | European Pat. Off. . |
| 867422 | 2/1953 | Fed. Rep. of Germany . |
| 1239266 | 7/1960 | France . |
| 483192 | 8/1979 | Spain . |
| 373516 | 1/1964 | Switzerland ........................ 128/92 |

*Primary Examiner*—David J. Isabella
*Attorney, Agent, or Firm*—Peter C. Richardson; Lawrence C. Akers; Elizabeth O. Slade

[57] ABSTRACT

A device for osteosynthesis comprises an elongated bone plate and an elongated slide plate adapted to be fitted on the outside of the bone plate. Several longitudinally spaced elongated holes for the reception of bone screws are provided in one longitudinally portion only of the bone plate, while the other longitudinal portion of the bone plate is provided with circular holes and the elongated slide plate is provided with several longitudinally spaced circular holes. The circular holes in the slide plate have a diameter approximately equal to the width of the elongated holes in the bone plate and a pitch substantially equal to the pitch of those elongated holes.

2 Claims, 1 Drawing Sheet

DEVICE FOR OSTEOSYNTHESIS

This is a continuation of application Ser. No. 07/233,954 filed on Aug. 18, 1988, now abandoned, which is a continuation of application Ser. No. 06/790,713 filed on Oct. 24, 1985, now abandoned.

BACKGROUND OF THE INVENTION

The invention relates to a device for osteosynthesis having several longitudinally spaced elongated holes for the reception of bone screws.

The simplest osteosynthesis plate is constituted by an elongated, flat, stiff plate element having one or two rows of circular holes, through which the bone screws are adapted to be screwed into the bone, in order to fixedly anchor the plate to the bone on both sides of the fracture surface. Such a plate, however, suffers from the disadvantage that the bores in the bone must be precisely set by the surgeon so that the plate may be neatly fitted. Otherwise the danger exists that the fracture surfaces, for example, may not lie one against another in a fixed relationship.

It has also become known in connection with osteosynthesis plates to use clamping devices, in order to build up a sufficient compression pressure between the fracture segments, prior to finally fixing the plate.

It has furthermore become known in connection with osteosynthesis plates to utilize elongated holes (French patent Letter No. 2 517 536 or German publication letter No. 2 806 414). Such elongated holes may be formed conically at the ends so that with the aid of bone screws the head of which is formed conically or crowned at the underside thereof, a pulling force may be exerted on the plate and, thus, on the fracture segments. Such osteosynthesis plates are also called compression plates. It is intended to generate with them a compression pressure in the fracture surface. What is disadvantageous with such plates is the fact that here as well the bores must be set very accurately by the surgeon, in order to be able to fully utilize the anyway relatively small path of adjustment. If, with respect to one elongated hole this path of adjustment is obtained only in part or not at all, it is no longer possible also with respect to the other elongated holes to generate any tension.

During the healing process, a so-called sintering of the fracture will occur, which may entail a shortening of the bone in this region. In order to make sure that the fixation with the aid of the osteosynthesis plate may follow this, the screws must move relative to the plate in the elongated holes. Between the screw head and the hole, however, there is essentially only a point contact taking place. By virtue of the high surface pressure at the contact points the screw head digs itself more and more into the material of the plate and causes an extraordinarily high coefficient of frictional adhesion which practically prevents the relative movement as described above being obtained with the normally occurring forces. Besides, it is not possible in this manner to apply to the bone screws a given torque in a manner to be capable of reproduction. The known osteosynthesis plates, in addition, are provided with elongated holes over the entire length thereof. Even if a relative movement is possible, a sort of floating retention or bearing of the plate will occur, finally abolishing the desired effect of fixation.

SUMMARY OF THE INVENTION

It is therefore the object of the invention to provide a plate for osteosynthesis which makes possible a stable fixation of the fracture segments while at the same time adapting itself to the relative displacement of the fracture segments essentially in parallel with the osteosynthesis plate.

This object is attained in accordance with the invention by arranging the elongated holes only in one longitudinal section of the plate, while providing circular holes in the other longitudinal section, and an elongated slide plate adapted to be fitted on the outer surface of the plate having longitudinally spaced circular holes the diameter of which approximately corresponds to the small diameter of the elongated holes, and the pitch of which corresponds of that of the elongated holes.

With the osteosynthesis plate according to the invention, only one longitudinal section is provided with elongated holes. Thereby, the plate is non-displaceably fixed at the bone on one side of the fracture with the aid of one or several bone screws. Associated with the longitudinal section having the elongated holes is a slide plate lying in close contact against the side of the plate facing away from the bone, said slide plate being provided with circular holes, the pitch of which corresponding to that of the elongated holes. The bone screws are passed through the circular holes of the slide plate and subsequently through the elongated holes, and screwed into the bone. Compression forces in a sufficient degree are applied between the screw heads and the slide plate on the one hand and the osteosynthesis plate on the other hand, so that with the normal loads, when the fracture segments are lying in abutting relationship against each other, a relative displacement between the said members will not occur. But if, due to fracture sintering, a gap however small should form in the region of the fracture surface, the slide plate by virtue of the relatively low surface pressure would make possible a corresponding displacement of adaptation. In this manner, an effective stabilization is provided also with such processes taking place in the fracture. Above all, it is obtained with the osteosynthesis plate according to the invention that the fracture segments are loaded with the natural surface pressure which is created with the movements of the patient perhaps in the femur or in the tibia. The osteosynthesis plate according to the invention thus makes possible a dynamic load of the fracture. A dynamic load of the fracture enhances the healing process considerably and allows the patient to use the broken bone again approximately in the normal extent within a relatively short period of time.

In another embodiment of the invention provision is made for the slide plate to be vaulted in a transverse direction and to come to lie against the plate by its concave side. The slide plate with such an embodiment develops a spring effect when being pressed against the osteosynthesis plate with the aid of the head of a bone screw. In this manner, a desired contact pressure may be adjusted relatively precisely and, thereby, also the relative compression force which is necessary, in order to obtain a displacement of the slide plate relative to the osteosynthesis plate.

Another embodiment of the invention provides for the plate to comprise a longitudinally extending channel which opens only to the outside and the bottom of which is provided with the elongated holes with the slide plate guided therein. When using a normal flat osteosynthesis plate the slide would be effective to cause a corresponding increase in the volume of the osteosynthesis aid and add to the danger tissue irritation. Positioning the slide plate in a channel reduces the increases in dimensions caused by the slide plate. But nevertheless, the surface inertia moment of the osteosynthesis plate is not influenced in a degree worth mentioning.

It is particularly advantageous if, in another embodiment of the invention, the osteosynthesis plate is shaped to be approximately U-shaped in configuration. So as to obtain a surface inertia moment approximately the same as in the case of flat osteosynthesis plates, the legs must indeed be selected to be slightly longer than the thickness of the known plate but, to make up for this, the slide plate which has a small thickness relative to the osteosynthesis plate is disposed in the channel in completely countersunk arrangement. As also the head of the bone screw is disposed in countersunk arrangement and projects above the outside only in a minimum extent, the overall dimension of the osteosynthesis aid in the direction of the bone screw axes is hardly greater or, even smaller, than with conventional osteosynthesis plates. Let it be mentioned at this juncture that it may be also be advantageous to use such an osteosynthesis plate according to the invention without a slide plate.

In order to reduce the danger of tissue irritations, provision is made in another embodiment of the invention for the height of the legs to decrease steadily towards the ends. At the ends, the necessary bending moment is known to decrease, so that a small surface inertia moment may be accepted. The height of the legs may then be correspondingly reduced.

So as to obtain a position in which it comes to lie in close contact against a hollow cylindrical bone, provision is made in another embodiment of the invention for the side of the plate associated with the bone to have a longitudinally extending groove.

DETAILED DESCRIPTION OF THE INVENTION

The invention will be explained in the following in more detail by way of drawings.

Figure 2:
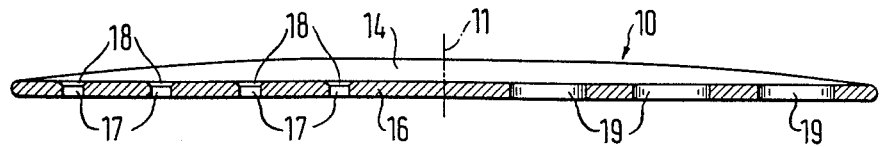
FIG. 2 shows a sectional view of the plate according to FIG. 1 taken along line 2—2.

Prior to enlarging in more detail on the individual representations shown in the drawings, it has to be stated that each of the features described is of inventively essential importance by itself or in connection with features of the claims.

The drawings are merely diagrammatic in nature and not to scale.

Figure 1:
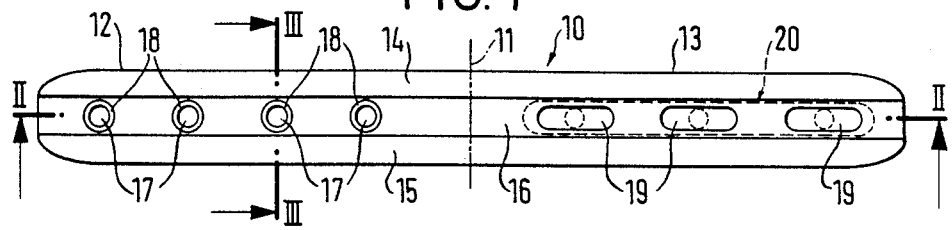
FIG. 1 shows a top plan view taken on a diagrammatic representation of the osteosynthesis plate according to the invention.
Figure 3:
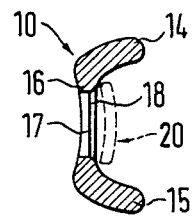
FIG. 3 shows a sectional view of the plate according to FIG. 1 taken along line 3—3.

FIGS. 1 to 3 show a relatively narrow elongated osteosynthesis plate generally designated with 10. Its length may differ between 200 mm (femur) and 125 mm (tibia), for example. The width may correspondingly be between 16 and 14 mm. The plate 10 is subdivided into a first longitudinal portion 12 and a second longitudinal portion 13 on both sides of a center line 11. As will be seen from an overall view of the FIGS. 1 to 3, the plate is U-shaped in cross section and thus comprises two legs 14, 15 and one web 16 disposed therebetween. As will be seen from FIG. 2, the height of the legs 14, 15 slightly decreases towards the ends.

Four circular holes 17 are formed in the bottom or the web 16 of the longitudinal portion 12 having their respective central points disposed on the longitudinal axis. They are equally spaced from each other and have a countersinking 18 on the side facing the legs 14, 15. The holes 17 are serving for the reception of known-per-se bone screws the head of which is in part received by the countersinking 18. The other longitudinal portion 13 has equally spaced elongated holes 19 of a length of 15 mm, for example. The elongated holes 19 are circularly rounded off at the ends thereof. The small diameter of the elongated holes 19 is dimensioned to be such that the bone screws may be passed through the elongated holes 19. The elongated holes 19 comprise a smooth paraxial wall without countersinking.

Figure 4:
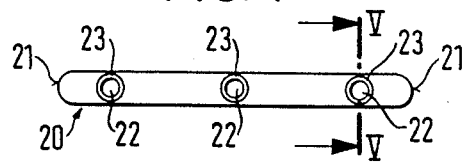
FIG. 4 shows a top plan view of the slide plate for an osteosynthesis plate according to FIGS. 1 to 3.
Figure 5:
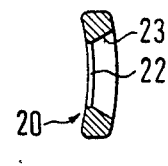
FIG. 5 shows a sectional view of the slide plate according to FIG. 4 taken along line 5—5.

FIGS. 4 and 5 show a slide plate 20 which may consist of the same material compatible with the human body as the plate 10. The slide plate 20 is by far thinner than the plate 10 (the sectional views according to FIGS. 3 and 5 are enlarged and do not represent this relation in thickness). While the web or bottom 16 may have a thickness of 2.8 to 3.4 mm, for example, the slide plate 20 has a thickness of about 1.5 mm. The slide plate 20 is rounded off circularly at the ends thereof as shown at 21. As will be noted form FIG. 5, the slide plate 20 is bent in a transverse direction. It has three circular holes 22 equally spaced from each other and having a diameter corresponding to the small diameter of the elongated holes 19. The circular holes 22 are provided with a countersinking 23.

In the process of application the end portion 12 of the osteosynthesis plate 10 is first fixed at the bone with the aid of bone screws (not shown) which are passed through the circular holes 17. Following this, the slide plate 20 is placed in the canal formed by the legs 14, 15 and the bottom 16, as indicated in broken lines in FIGS. 1 and 3. The pitch of the holes 22 of the slide plate 20 corresponds to the pitch of the elongated holes 19. Bone screws are screwed into the bone through the the circular holes 22 of the slide plate 20 and through the elongated holes 19, after the fracture segments have been aligned. The bone screws and holes 22, respectively, of the plate 20 are arranged in such a manner as to come to lie possibly close to the right-hand end, in FIG. 1, of the elongated holes 19. The head of the bone screws presses the slide plate tightly against the bottom 16, with the slide plate 20 resiliently deforming and the vault in part disappearing. Through a corresponding torque of 2.5 Nm, for example, at the bone screws a sufficient compression is maintained between the members, in order to obtain a sufficient stabilization of the fracture. The maximum surface pressure, however, is relatively low, so that the bone screws may move in the elongated holes when the fracture segments are approaching each other more closely. Such a relative movement of the bone screws, however, is coupled to a displacement of the slide plate 20. On the basis of the relatively low surface pressure the slide plate may slide in the channel of the plate 10 under a corresponding friction.

It goes without saying that all the edges of the plate 10 and the slide plate 20 are sufficiently rounded off so as to preclude tissue irritations as far as possible.

We claim:

1. A device for osteosynthesis comprising:

(a) an elongated bone plate having first and second longitudinal portions and having a bottom surface and an upper surface, said bottom surface being adapted to rest upon the patient's bone, said upper surface being oppositely disposed with respect to said bottom surface, with a plurality of elongated holes disposed in a longitudinally spaced arrangement for the reception of bone screws being provided in said second longitudinal portion of said bone plate, and a plurality of circular holes for the reception of bone screws being provided in said first longitudinal portion, and said first longitudinal portion being adapted to be screwed into the patient's bone on a first side of a fracture, and said second longitudinal portion being adapted to be screwed into the patient's bone on a second side of the fracture, and (b) an elongated plate having an upper surface and a bottom surface which is adapted to be fitted on and slidable with respect to the upper surface of, and only on said second longitudinal portion of, said bone plate and provided with a plurality of longitudinally spaced circular holes each having a center and having a diameter approximately equal to the width of said elongated holes and a separation between two adjacent centers being substantially equal to the separation between the centers of two adjacent elongated holes, wherein said slide plate is curved in its transverse cross-section with the concave side of the slide plate being adapted to lie in close contact against said bone plate when the slide plate is fitted on the bone plate, wherein said bone plate defines a longitudinally extending channel having a channel bottom and opening towards the upper surface of the bone plate, with said elongated holes being located on said channel bottom and said slide plate being received and guided within said channel when the slide plate is fitted on the bone plate, wherein said bone plate has an approximately U-shaped transverse cross-section with the shape of said U-shaped transverse cross-section being formed from legs having a height h, and wherein said bone plate has an upper surface exhibiting a tapered profile in the longitudinal direction with said height h of said legs of said U-shaped cross-section steadily decreasing from the center of said bone plate to the ends of said bone plate.

2. A device for osteosynthesis comprising:

(a) an elongated bone plate having first and second longitudinal portions and having bottom and upper surfaces, said bottom surface being adapted to rest upon the patient's bone, said upper surface being oppositely disposed with respect to said bottom surface, with a plurality of elongated holes disposed in a longitudinally spaced arrangement for the reception of bone screws being provided only in said longitudinal portion of said bone plate, and a plurality of circular holes for the reception of bone screws being provided in said first longitudinal portion, and (b) an elongated slide plate having an upper surface and a bottom surface which is to be fitted on the upper surface of said bone plate and provided with a plurality of longitudinally spaced circular holes each having a center and having a diameter approximately equal to the width of said elongated holes and a separation between two adjacent centers being substantially equal to the separation between the centers of two adjacent elongated holes, wherein said slide plate is curved in its transverse cross-section with the concave side of the slide plate adapted to lie in close contact against said bone plate when the slide plate is fitted on the bone plate, wherein said bone plate defines a longitudinally extending channel having a channel bottom and opening towards the upper surface of the bone plate, with said elongated holes being located at said channel bottom and said slide plate being received and guided within said channel when the slide plate is fitted on the bone plate, wherein said bone plate is approximately U-shaped in its transverse cross-section, wherein the U-shape is formed from legs having a height h and wherein said bone plate has an upper surface exhibiting a tapered profile in the longitudinal direction wherein said height h of said legs of said U-shaped cross-section steadily decreases from the center of said bone plate to the ends of said bone plate.

* * * * *